US012508450B1

(12) United States Patent
Dewispelaere et al.

(10) Patent No.: US 12,508,450 B1
(45) Date of Patent: Dec. 30, 2025

(54) ANTIVIRAL MOBILE RESPIRATORY PERSONAL PROTECTION DEVICE

(71) Applicants: Jeffrey Richard Dewispelaere, Elk River, MN (US); Frank Edward Kaczmarek, Ivanhoe, MN (US)

(72) Inventors: Jeffrey Richard Dewispelaere, Elk River, MN (US); Frank Edward Kaczmarek, Ivanhoe, MN (US)

(73) Assignee: Jeffrey Richard Dewispelaere, Elk River, MN (US)

( * ) Notice: Subject to any disclaimer, the term of this patent is extended or adjusted under 35 U.S.C. 154(b) by 867 days.

(21) Appl. No.: 17/745,746

(22) Filed: May 31, 2022

(51) Int. Cl.

| | |
|---|---|
| ***A62B 9/00*** | (2006.01) |
| ***A61L 9/16*** | (2006.01) |
| ***A62B 18/04*** | (2006.01) |
| ***A62B 18/10*** | (2006.01) |

(52) U.S. Cl.
CPC ................ *A62B 9/003* (2013.01); *A61L 9/16* (2013.01); *A62B 18/045* (2013.01); *A62B 18/10* (2013.01)

(58) Field of Classification Search
CPC ....... A62B 7/00–12; A62B 9/00; A62B 9/003; A62B 9/02–027; A62B 9/04; A62B 17/00–08; A62B 18/00–10; A61L 9/16–22
USPC ............ 128/201.25, 202, 19, 204.15, 17–18, 128/205.12, 25, 27, 206.12, 23–24
See application file for complete search history.

(56) References Cited

U.S. PATENT DOCUMENTS 4,549,541 A * 10/1985 Sundahl ................. A62B 18/04
2/2.5

FOREIGN PATENT DOCUMENTS

| | | | | | |
|---|---|---|---|---|---|
| CN | 111493421 | A | * | 8/2020 | ......... A41D 13/0053 |
| CN | 111921111 | A | * | 11/2020 | ............... A62B 7/10 |
| EP | 2818204 | A1 | * | 12/2014 | ........... A62B 17/005 |
| EP | 2509687 | B1 | * | 4/2019 | ............... A62B 7/02 |
| WO | WO-2021189150 | A1 | * | 9/2021 | ............... A61L 9/16 |
| WO | WO-2023043985 | A1 | * | 3/2023 | ............... A62B 7/10 |

OTHER PUBLICATIONS

Translation of CN 11192111. (Year: 2020).*
Translation of EP 2818204. (Year: 2014).*
Translation of CN 111493421. (Year: 2020).*

* cited by examiner

*Primary Examiner* — Paige Kathleen Bugg

(57) ABSTRACT

Invention is described which sterilizes air contaminated with airborne virus by means of superheating the air to over 400 Fahrenheit then cooling air to breathable temperatures. The invention disposes a fan pushing contaminated air into a positive temperature coefficient semiconductor heater to superheat the air which is subsequently cooled by a two stage cooling system. First stage of the cooling system is an air-to-air heat exchanger using ambient air from second fan to cool the superheated air. The second stage of cooling is provided by a solid-state Peltier heat pump which further transfers heat energy to ambient air provided by a third fan. Invention is disposed onto a sealed helmet which the sterilized air is conveyed causing an overpressure to eliminate the possibility of contaminated air entering the helmet. The invention is entirely reusable after use in a contaminated environment and does not rely on filters to remove airborne virus.

7 Claims, 7 Drawing Sheets

ANTIVIRAL MOBILE RESPIRATORY PERSONAL PROTECTION DEVICE

BACKGROUND—PRIOR ART

US Patents

| Patent Number | Kind Code | Issue Date | Patentee |
|---|---|---|---|
| U.S. Pat. No. 8,667,959 | | Mar. 11, 2014 | Tilley |
| U.S. Pat. No. 4,886,056 | | Dec. 12, 1989 | Simpson |
| U.S. Pat. No. 6,435,184 | | Aug. 20, 2002 | Ho |
| US 2013/0174845 | | Jul. 11, 2013 | Vinnakota |
| US 2006/0076012 | A1 | Apr. 13, 2006 | Tanizawa |
| U.S. Pat. No. 7,543,584 | B2 | Jun. 9, 2009 | Brookman |
| U.S. Pat. No. 9,248,248 | B2 | Feb. 2, 2016 | Virr |
| U.S. Pat. No. 4,462,399 | | Jul. 31, 1984 | Braun |
| U.S. Pat. No. 3,822,698 | | Jul. 9, 1974 | Guy |
| US 2009/0314295 | A1 | Dec. 24, 2009 | Hatmaker |
| U.S. Pat. No. 6,494,940 | B1 | Dec. 17, 2002 | Hak |

The present invention relates generally to reusable personal protection equipment that provides sterilized and dry breathable air in hazardous environments which contain airborne virus and more specifically to a self-contained and individually wearable system comprising an integrated continuous air flow system of air heating, air sterilization, staged air cooling, quick don head gear, safety controls, and battery electrical power.

Frequently, medical personnel and others require protection against the risk of infectious airborne virus that are communicable and present various health risks. This is commonly referred to as Personal Protection Equipment (PPE) and is usually intended to be all or in part disposable after a single use upon exposure to a hazardous viral environment. The present invention is completely reusable and does not rely on a disposable filter element to provide effective personal protection against airborne virus hazards.

In the case of a large-scale pandemic, each medical person may require multiple changes of the prior art disposable PPE elements per day driving the need for several million sets of PPE per day in a given geographic region. Thus, the existing disposable PPE becomes a continuous and severe logistical risk involving the large-scale supply, distribution, and disposal of PPE after use. In the case of a long-term pandemic lasting more than a few months these logistical challenges become progressively worse. Should the demand exceed supply at a medical facility, then compromises and alternatives are used which are less effective and substantially increase the risk that medical personnel will be exposed to the airborne viral agents and be incapacitated or become infectious disease carriers. Additionally, in the case where there is a medical emergency that requires quick response from unprotected medical personnel, the existing PPE can be slow to don due to the many individual elements and fitting challenges.

The present invention solves these problems by providing a completely reusable and self-contained solution that conveys safe sterilized dry air to a wearer working in an environment that is contaminated with airborne virus and thus enables a person to be highly mobile while performing various tasks free of any external power or air supply systems. The present invention enables eye, head, and respiratory protection from viral agents and is designed to be fully reusable, effective, comfortable, and quick to don. This invention is further compatible with protective coveralls, gloves, and boots.

The prior art addressing this need can be broken into two main approaches. The first of these approaches is the most common and includes an ensemble of a separate a filtration mask, face shield or eye protection, and a flexible enclosure for the remainder of the head. The simple filtration mask is passive and operates by providing a filter barrier of appropriate effectiveness such that virus particles are trapped on the outside of the filter as the wearer breathes. While the entrapment of the virus particles on the outside of the filtration mask prevents them from being inhaled into the wearers respiratory system, there is a subsequent infection risk that the wearer or others touch the exterior of the filtration mask to remove it, handle it, or dispose of it. The entrapment of the virus into the material of the mask makes it impossible to confidently sanitize once used therefore the used and contaminated filtration mask becomes a bio-hazard requiring careful disposal. Additionally, the seal of these masks onto the face of the user can be imperfect and can therefore present the risk of viral agent pathway to the user. Eye protection for the protective ensemble usually consists of goggles or a full-face shield typically made of clear plastic. The air seal on the eye protection is often considered less critical and so by design there are air pathways that nonetheless present the risk of an infection pathway. While this type of eye protection can be washed to sanitize them, this is cumbersome and they are most often disposed of after use. Finally, the ensemble includes a head enclosure normally consisting of a flexible hood with a drawstring to provide a limited seal against virus particles settling on the hair or scalp. The hood could also be washed to be sanitized, but is also most often disposed of because such a task is cumbersome and poses an infection risk due to handling of contaminated gear.

In addition to the logistics of providing this PPE on a frequent basis, fogging of the eye protection is an issue. This fogging is caused by warm moist exhaled breath from the wearer which can escape from the mask and fog the eye protection.

The second prior art approach is commonly known as a Powered Air Purifying Respirator (PAPR) which is a powered breathing apparatus that provides purified air by means of mechanically forcing contaminated air through a filtration system and sometimes additionally using ultraviolet light to kill the virus. This system usually contains a powered fan which ingests external contaminated air and by means of channels and tubes guides the air through a replaceable filtration barrier to entrap virus particles similar to a face mask. The air thus sanitized of virus particles is conveyed to a sealed helmet or soft headgear and mask. This system is normally battery powered although electrical power provided by an electrical power cord is an alternative in some settings. While having comfort advantages over the first approach this system is two orders of magnitude more expensive than the first approach. When used in an environment with airborne virus, much of the system can be sanitized and hence reused, but the filtration barrier suffers the same logistical challenge of the simple filtration mask in that once used it is considered contaminated. While the filter may be capable of additional use, from a practical standpoint it cannot be stored as it is contaminated and represents an infection hazard. Therefore, the PAPR filters would need to be disposed of regularly and are currently expensive enough to be approximately 20% of the cost of the entire PAPR system. Finally, the fogging disadvantage of the first approach is magnified in a powered air purifying respirator due to the sealing of the integrated mask and eye protection.

Thus, prior art embodiments have one or more of the following disadvantages: logistical challenges due to lack of reusability, lowered effectiveness due to the risk of improper fit, fogging of eye protection, slow to put on, and cost. The present invention solves all of these problems and has the ability to provide purified air even in the most extreme virus contamination environment. It is quick to put on, enables high confidence of effectiveness, eliminates eye protection fogging, and most importantly is fully reusable. It is applicable to a variety of configurations corresponding to a wide range of pandemic personal protection settings. This teaching includes the physical and functional embodiments of the said invention.

SUMMARY OF THE INVENTION

The present invention inducts contaminated air, then sterilizes the air by super heating the air to temperatures above 400 degrees Fahrenheit, then cools the air by means of a two-stage cooling system before being supplied to the wearer. The invention has a closed loop control system to ensure that air is sterilized, that the helmet is not allowing contaminated air to reach the wearer, and that safe operation is maintained. The heating of the air in the invention is accomplished with a Positive Temperature Coefficient (PTC) semiconductor thermistor heater which heats the contaminated ambient air to a temperature above 400 degrees Fahrenheit. It is a medical fact that most viruses cease life functions above approximately 160 F however, in this invention, the active virus is killed by heating to temperatures such that the virus cell ruptures and ceases to be a functioning lifeform. This enables a compact sterilization system, however, the air thus heated is thermally unsafe to breathe. This invention solves this problem and enables the use of a PTC semiconductor thermistor heater to efficiently sterilize the air which is subsequently cooled to enable system weights and volumes such that the invention can be placed into a self-contained and individually wearable system worn by an individual without the need for any external power or support systems.

It is an object of this invention to provide a device for providing safe sterilized air to a person working in a virus contaminated environment by ingesting the contaminated air then superheating this air to above 400 degrees Fahrenheit to sterilize the virus contaminated air with heat by means of a continuous airflow directed across a Positive Temperature Coefficient (PTC) semiconductor thermistor heater whereby the superheated air is and subsequently cooled to breathable temperatures by a two stage system of an air-to-air heat exchanger and a Peltier heat pump before being conveyed into a positive pressure helmet or other wearable system.

It is an object of this invention to contain the device in a self-contained wearable mobile system that is completely reusable.

It is an object of this invention to contain the device in a self-contained wearable mobile system powered by rechargeable battery or batteries that provides several hours of use free of any external power supply, air supply, or control system.

It is an object of this invention to provide an efficient device in which the PTC semiconductor thermistor heater system eliminates moisture accumulation inside of the Antiviral Mobile Respiratory Personal Protection Device and hence eliminates fogging as an issue.

It is an object of this invention to provide control and safety with control feedback from five temperature probes in the air pathway to ensure the effective sterilization of the air and safe breathing temperatures, an oxygen sensor inside of the helmet to detect unsafe oxygen levels, and a an air pressure sensor inside of the helmet to detect positive pressure inside the helmet to ensure no inflow of contaminated air into the helmet.

It is an object of this invention to provide an electrical architecture which enables ingesting ambient contaminated air from outside the invention, then superheating heating said air to kill the virus by means of continuous airflow directed across a semiconductor thermistor heater whereby the superheated air is and subsequently cooled to breathable temperatures by a staged system of an air-to-air heat exchanger and a Peltier heat pump with closed loop control using a temperature, oxygen, and pressure feedback system.

It is an object of this invention to provide a display to the wearer which indicates sterilization functionality, helmet oxygen, helmet pressure, and battery life.

It is an object of this invention to provide a device that can be donned and be operational within 30 seconds.

Advantages

Accordingly, several advantages of one or more aspects of the Antiviral Mobile Respiratory Personal Protection Device embodiment are as follows:

- a system that provides effective protection to a wearer from hazardous airborne virus and is completely reusable in a system that is self-contained, wearable, and free of any external power or air supplies,
- a means to use a high temperature PTC semiconductor thermistor heater to kill airborne virus with temperatures above 400 F and does not rely on filters to protect the wearer from airborne virus biohazards,
- a personal mobile air sterilizer that can be confidently donned by the average person in under 30 seconds,
- a personal mobile air sterilizer that eliminates moisture accumulation such as fogging inside the apparatus and most particularly the eye protection such as helmet visors,
- a personal mobile air sterilizer that provides realtime feedback on the effectiveness of the invention virus protection for the wearer.

Conclusion, Ramifications, and Scope

Accordingly, the reader will see that the Antiviral Mobile Respiratory Personal Protection Device invention described herein is novel in the field of PPE used in environments with hazardous airborne virus. It is completely reusable and does not rely on any disposal single use components and is therefore free from the need of a daily logistics supply chain as required by disposable PPE. The invention is enabled by the use of a high temperature heater in a compact system which kills airborne virus by super heating the air to over 400 F and then cooling the thus sterilized air to breathable temperatures via a staged cooling system which uses an air-to-air heat exchanger and a Peltier Heat Pump. Importantly, the invention also inherently provides dry air to the user to eliminate moisture condensation inside the invention which eliminates a major problem in prior art.

The present invention can be utilized wherever a person experiences a hazardous environment that includes airborne virus in order to improve comfort, safety, performance, and confidence. Furthermore, the Antiviral Mobile Respiratory Personal Protection Device has additional advantages of being manufacturable, adaptable to a variety of price points, adaptable to a variety of material technologies, and adaptable to a wide range of embodiments such as the entire system contained in a helmet or the entire system distributed over the user's body.

Although the description above contains many specificities, these should not be construed as limiting the scope of the invention but as merely providing illustrations of several possible embodiments. For an example, the invention can be adapted to a mask only system or one that utilizes standard wall outlet electrical power instead of a battery or to provide sterilized dry air to hospital rooms or incubators. The scope of the embodiments should be determined by the appended claims and their legal equivalents, rather than by the examples given.

DRAWINGS—REFERENCE NUMERALS

DETAILED DESCRIPTION

This invention disposes a Positive Temperature Coefficient (PTC) semiconductor thermistor heater to heat contaminated air in a first cool, contaminated ambient air stream to a temperature of over 400 degrees Fahrenheit. This temperature of over 400 degrees Fahrenheit in combination with the time at this temperature in the invention's residence duct causes physical rupture of a pathogen cell structure and therefore renders the pathogen to a state that does not pose a health risk. The air so heated is named here heated sterilized air and although sterilized, it is too hot to safely breathe as it would cause thermal injury to a person. In the invention herein, the heated sterilized air is then cooled by means of two stages of cooling to a temperature that is safe and comfortable for breathing. In the first stage of cooling, an air-to-air heat exchanger cools the heated sterilized air by the transfer of heat energy from the heated sterilized air to a second cool, contaminated ambient air stream. In the invention, the heated sterilized air thus cooled is called here lower intermediate temperature sterilized air. In the second stage of cooling, a solid-state Peltier heat pump transfers heat energy from the lower intermediate temperature sterilized air to a third cooled, contaminated ambient temperature air stream which further cools the sterilized air down to a safe breathable temperature. The air thus cooled is called here final air temperature sterilized air and is provided to the wearer for breathing. A system of three variable speed fans is used to provide required air flow in the invention. The first fan provides air flow from the contaminated external ambient environment into the PTC semiconductor thermistor heater and after cooling, provides positive air pressure to the helmet. The second fan provides air flow from the contaminated external ambient environment to the air-to-air heat exchanger for the first stage of cooling. The third fan provides air flow from the contaminated external ambient environment to the Peltier hot side to form the second stage of cooling.

Figure 1:
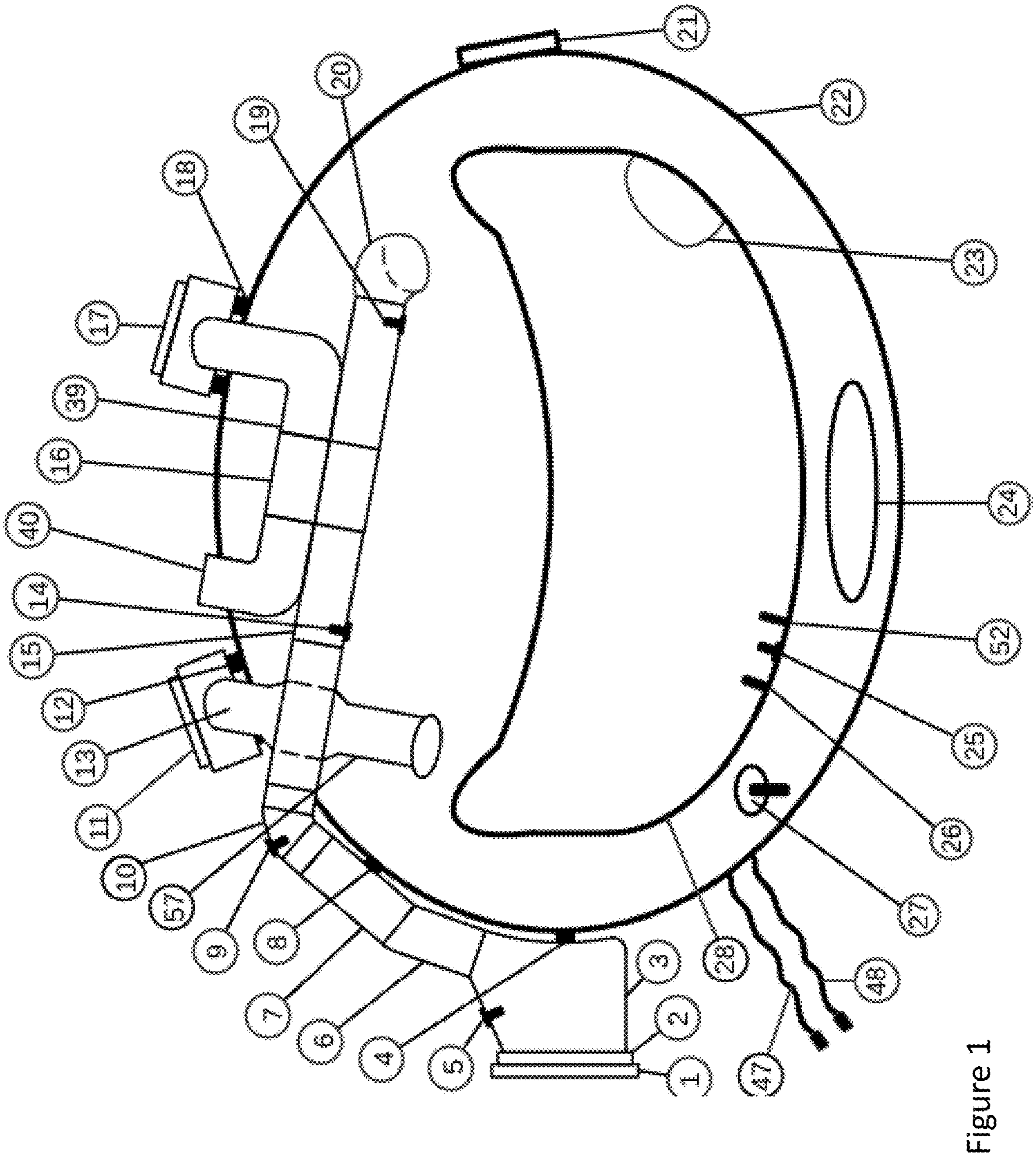
FIG. 1 is a top view perspective view of invention.

This invention is shown in FIG. 1 integrated with a helmet structure (22) where contaminated environmental air is drawn into the invention through a coarse screen (1) and optional HPEA filter (2) by the action of the first fan (3) which is mounted to the helmet structure with a vibration mount (4). The ambient environmental air temperature flowing into the invention is measured by a temperature probe (5) and used by the control system. The contaminated air then flows via (6) into the PTC semiconductor thermistor heater (7) to be superheated to above 400 degree Fahrenheit.

The PTC semiconductor thermistor heater (7) is mounted to the helmet structure by a thermally insulated mount (8). The air temperature at exit from the PTC semiconductor thermistor is measured by a temperature probe (9) and used by the control system for safe operation.

The exit airflow from the PTC semiconductor thermistor heater (7) called heat air flows into the residence duct (10). The length of the residence duct (10) in combination with the heated airflow speed determines the residence time of the heated air prior to stage one cooling. This residence time in combination with the temperature above 400 degrees Fahrenheit renders the virus non-functional. Therefore, the residence duct length (10) is designed to provide the required residence time at temperature for effective virus elimination. The air exiting the residence duct in the invention is here called heated sterilized air as the air has been both heated to a temperature above 400 degrees Fahrenheit to accomplish sterilization.

Continuous air flow is integral to the use of PTC semiconductor thermistor heaters for this invention. This continuous air flow combined with heated air temperature above 400 degrees Fahrenheit also dries the air and so eliminates moisture accumulation as an issue in or outside of the invention.

The first stage air cooler is an air-to-air heat exchanger (13) with a second ambient temperature airflow heat sink provided by the second fan (11). The second fan (11) is affixed to the helmet via vibration mount (12). The heated sterilized air enters the air-to-air heat exchanger via residence duct (10) and exits via intermediate duct (15). The air-to-air heat exchanger (13) must be insulated due to the safety risk from the surface temperature of the heat exchanger. The heat energy taken from the heated sterilized airflow is exhausted to the environment externa helmet by duct (57). The intermediate duct (15) is also insulated to reduce the safety risk from the hot surface of the intermediate duct. The lower intermediate temperature sterilized air exiting from the air-to-air heat exchanger in the intermediate duct (15) is measured by a temperature probe (14) and used by the control system for safe operation.

The lower intermediate temperature sterilized air in the intermediate duct (15) after the stage of cooling is still too hot to safely breath until it flows through the second stage cooler which consists of a Peltier Heat Pump (16) contained in a bi-duct reverse flow arrangement. The Peltier Heat Pump moves heat energy from the incoming lower intermediate temperature sterilized air to the third cool, contaminated ambient air flow supplied via the third fan (17) which is affixed to the helmet structure via a vibration mount (18). The third cool, contaminated ambient air flow is in reverse flow to the lower intermediate temperature sterilized air flow direction and is exhausted to the external environment by duct (40). The second stage of cooling creates the final air temperature sterilized air in the invention.

The air exiting Peltier Heat Pump through the final duct (20) is final air temperature sterilized air and is measured by a temperature probe (19) which is used by the control system for safe operation.

The final air temperature sterilized air flows into the airspace inside the helmet structure via duct (20). This over-pressurizes the helmet in order to always maintain an outflow of sterilized air from the helmet which eliminates potential inflow of external contaminated air to the inside of the helmet. This over pressurization is controlled via a one-way pressure valve (21) such that no external contaminated air can flow into the helmet, but at a preset pressure, sterilized air is released into the external environment such as when the user exhales. A display (23) of system parameters including sterilization status is provided so that the user can easily and continuously view the status while wearing the helmet.

The helmet interior air temperature is measured by a temperature probe (25) and used by the control system for safe operation. A system power on/off switch (27) is provided near the front of the helmet to be easily accessible to the user. The helmet air oxygen level is measured by a probe (52) and monitored by the control system to indicate safe operation to the user. The helmet air pressure level is measured by a probe (26) and is used by the control system for safe operation. The helmet is sealed with a clear visor (28). Electrical power is provided via quick disconnect power cable (48) from a battery. Radio communications to the helmet is provided via a quick disconnect signal cable (47).

As it is anticipated that the invention will be used in a medical environment where voice communication is important, a sealed acoustic membrane (24) is provided near the mouth area so that sound energy from the users voice is transmitted to the external atmosphere.

Figure 2:
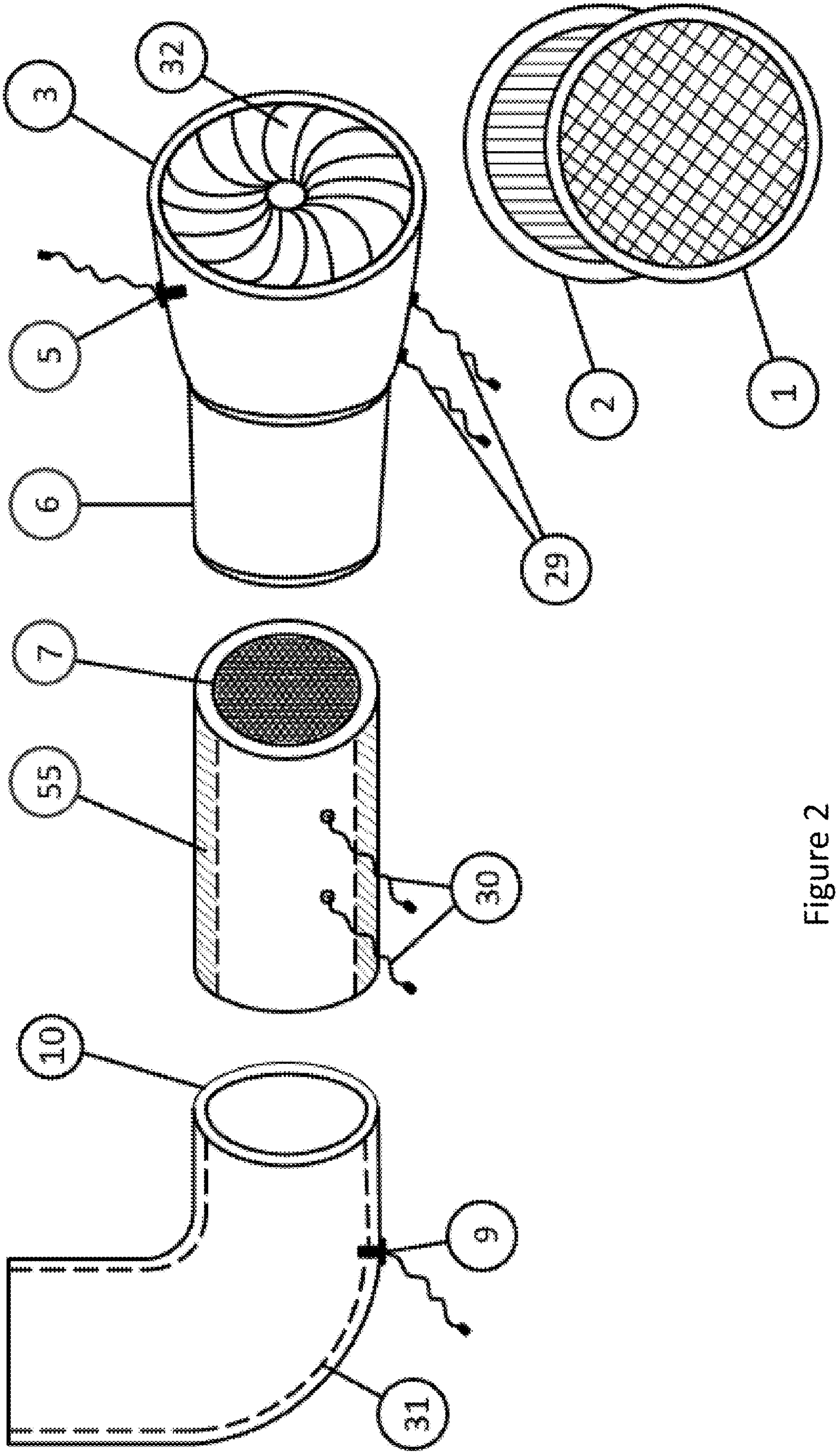
FIG. 2 is an isometric exploded view of the PTC air heater sub-system.

FIG. 2 shows further detail of the air heater subsystem. The external contaminated air is ingested into the system through a coarse screen (1) which prevents objects such as fingers, medical curtains, and paper from entering the system. Centrifugal fan (3) has entrance to the impeller (32) oriented to face away from the helmet. The ambient temperature probe (5) is placed at the entrance to the fan such that incoming air flows over the temperature probe. The fan is powered by wires (29) which contain electrical positive and negative. The fan (3) causes the first stream of cool, contaminated air to flow through connecting duct (6) and into the PTC heater (7). The PTC heater (7) has the heater elements arranged in a honeycomb form for maximum heat transfer to the air while limiting pressure loss. The PTC heater is provided with insulation (55) disposed on the exterior to provide a safe surface temperature as the PTC exterior surface temperature is above 400 degrees Fahrenheit and is therefore a safety hazard. The PTC heater is powered by wires (30) which contain electrical positive and negative. The heated air exiting from the PTC Heater (7) flows into the residence duct (10) which is also insulated (31) to provide safe exterior temperatures and reduce heat loss to the ambient environment. The length of the residence duct (10) provides the necessary time at temperature to render the airborne virus organism non-functional.

Figure 3:
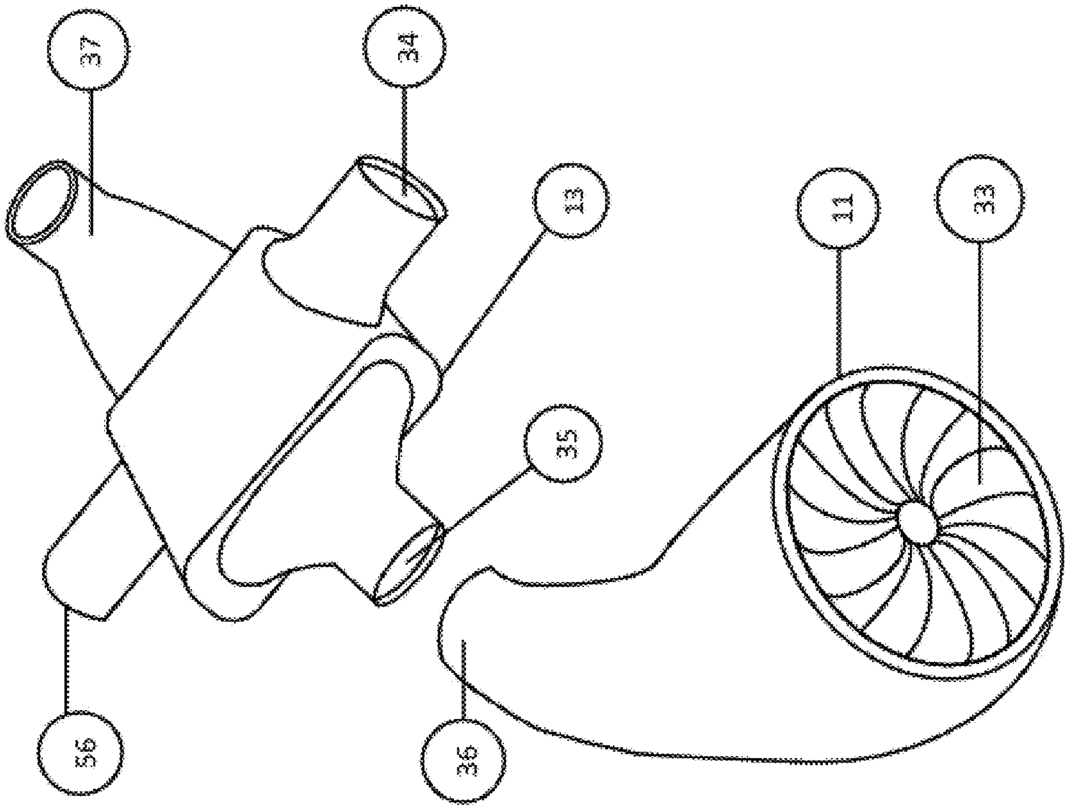
FIG. 3 is an isometric exploded view of the first stage cooling sub-system utilizing an air-to-air heat exchanger.

FIG. 3 shows further detail of the first stage of the inventions cooling system. The second stream of cool, contaminated ambient air is ingested via a centrifugal fan (11) through the fan impeller face (33). The exit flow from this fan flows through a collector (36) and into the air-to-air heat exchanger heating passage through an entrance fitting (35). Heat energy is transferred from the heat sterilized air to the second stream of cool, contaminated ambient air in the heat exchanger (13) and exhausted externally to the environment through a vent (37). The heat sterilized air enters the air-to-air heat exchanger (13) from the residence duct (10) through a fitting (34) and is exhausted at as lower intermediate temperature sterilized air through a fitting (56) into duct (15).

Figure 4:
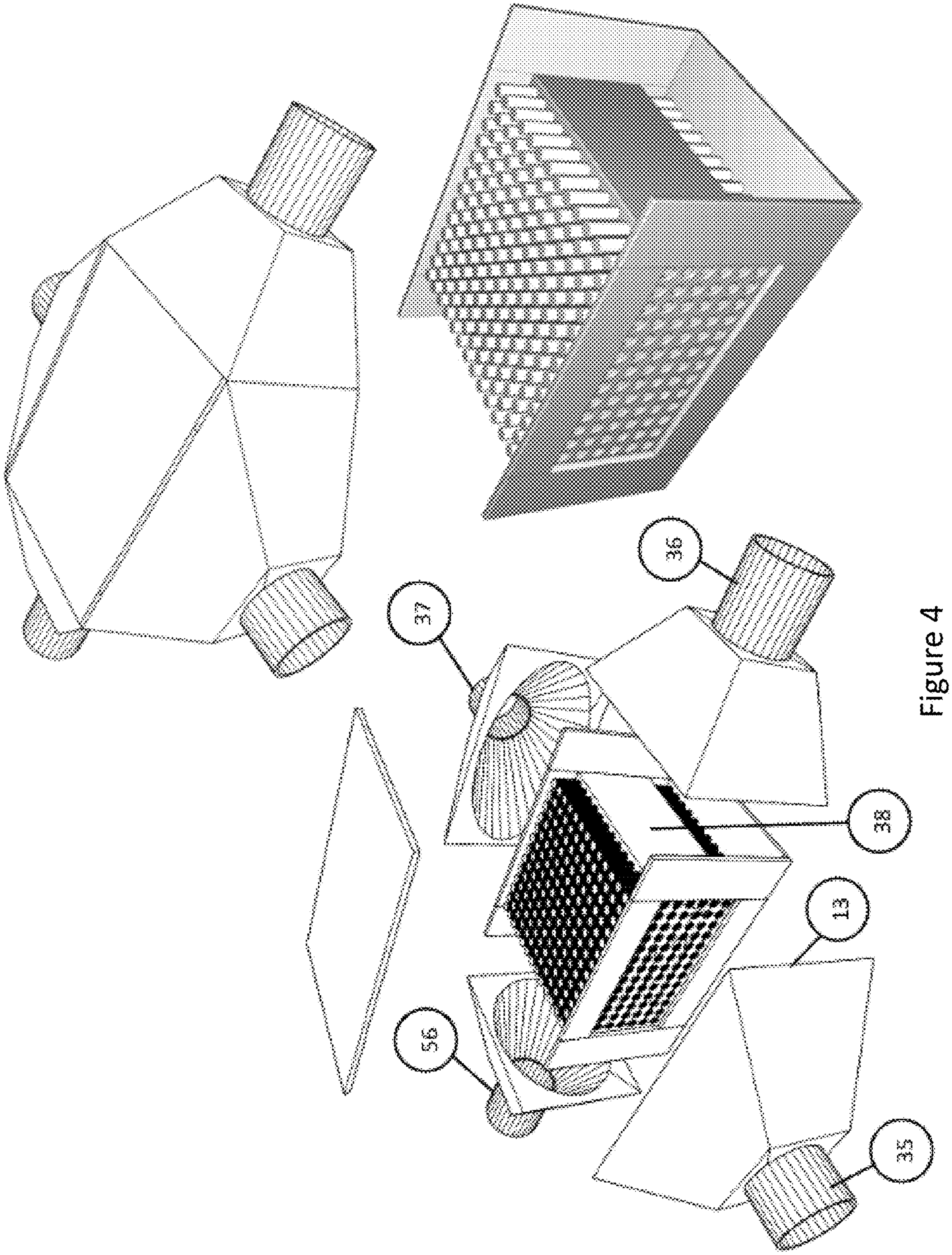
FIG. 4 is a detailed internal view of the air-to-air heat exchanger used in the first stage cooling subsystem.

FIG. 4 shows the interior detail of the air-to-air heat exchanger (13) which forms the first stage of the inventions cooling system. A second cool, contaminated ambient air stream proceeds through an entrance fitting (35) and flows through thermally conductive channels (38) which isolates the heated sterilized air flow (36) from the second cool, contaminated ambient air used for cooling. As the heated sterilized air flows through the thermally conductive channels (38) the heat energy is transferred from the heat sterilized air to the second cool, contaminated ambient air. Therefore the heated sterilized air temperature is reduced as it flows towards exit fitting (56) to form intermediate lower temperature sterilized air. Conversely the second cool, contaminated ambient air temperature is increased in the air-to-air heat exchanger as it flows towards the vent (37). Thus, heat from the sterilization process is transferred to the external ambient environment.

Figure 5:
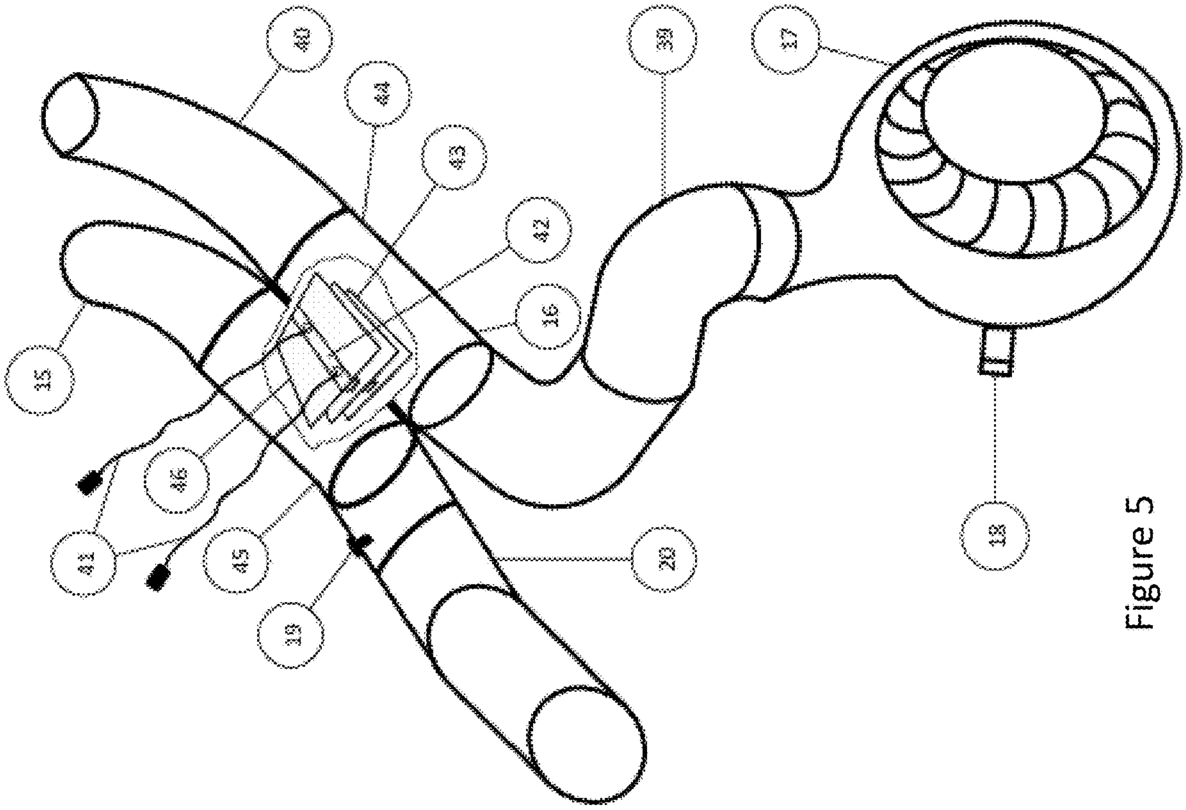
FIG. 5 is an isometric internal view of the second stage cooling sub-system utilizing a Peltier solid state heat pump.

FIG. 5 shows further detail of the second stage (16) of the inventions cooling system. The intermediate lower temperature sterilized air entering the second stage is still above safe breathing temperatures, but does not possess sufficient temperature differential in comparison to the ambient air to efficiently cool it via an additional air to air heat exchanger. Additionally, for comfort reasons the ability to cool to air temperatures below ambient is required. Therefore, the inventions second stage cooling system uses a solid-state Peltier heat pump (42) which transfers heat from the intermediate lower temperature sterilized air to the ambient atmosphere. The intermediate lower temperature sterilized air from the first stage cooling system enters the second stage cooling system through intermediate duct (15) and flows across cooling fins (46) that are cooled by a Peltier heat pump (42). The air thus cooled makes final air temperature sterilized air that is both a comfortable breathing temperature and is sterilized. The final air temperature sterilized air flows into the helmet through a final duct (20) with the air temperature being measured by a temperature probe (19).

The Peltier heat pump (42) is positioned between two counter-flowing air ducts to transfer heat energy from the intermediate lower temperature sterilized air in the sterilized air flow duct (45) to the third cool, contaminated air provided through a duct (44). A centrifugal fan (17) mounted to the helmet with a vibration mount (18) ingests a third cool, contaminated ambient air stream which is then directed through a duct (39) going into the second stage cooling unit (16). This third cool, contaminated ambient air then flows across Peltier hot side heat transfer fins (43). The heat energy from the intermediate temperature sterilized air is transferred into this air stream and is therefore transferred into the external environment through an exhaust duct (40).

The second stage cooling system heat transfer is modulated by the electrical power provided by wires (41) from a closed loop control system utilizing the second stage exit temperature probe (19). Thus controlled, the invention can safely operate across a range of ambient temperature conditions.

Figure 6:
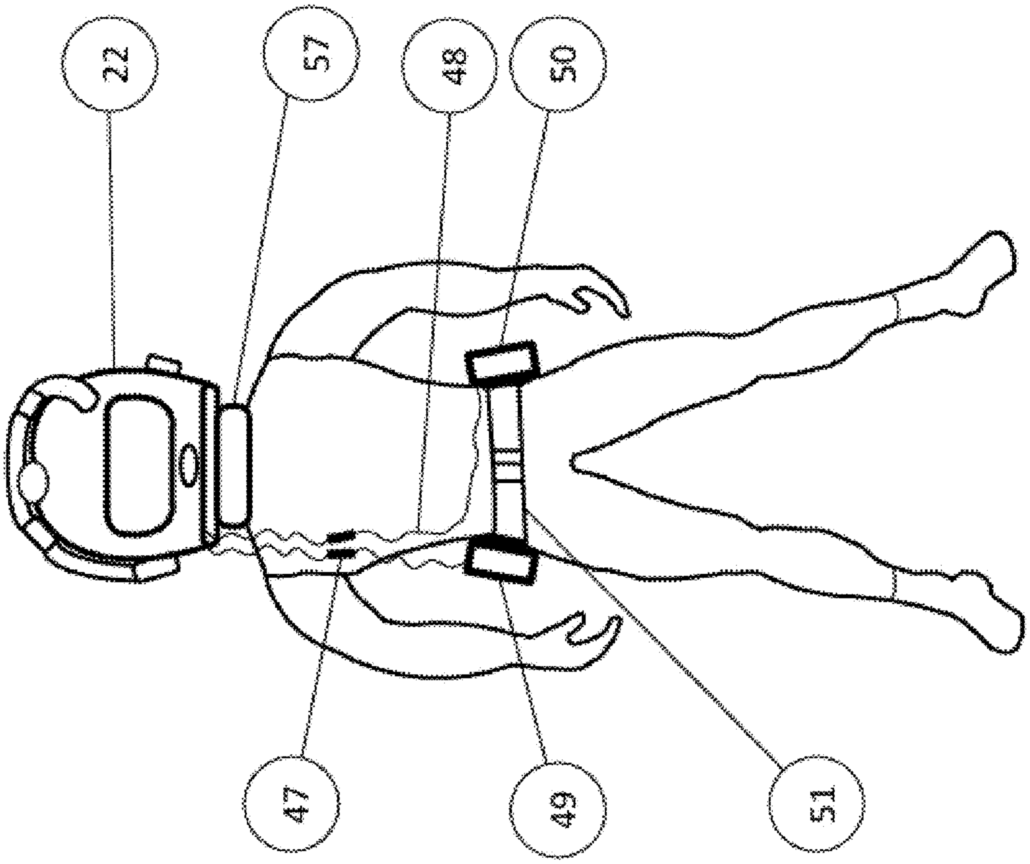
FIG. 6 is a view of the invention as worn by a user.

The entire invention as worn by a person is shown in FIG. 6. The helmet (22) has an elastic neck shroud (576) which lightly seals to the users neck or hazardous material suit. An electrical cable (47) connects the helmet to a radio communication device (49) worn on a belt (51). A further electrical cable (48) provides electrical power to the helmet (22) via battery (50) which is also worn on the same belt (51).

Figure 7:
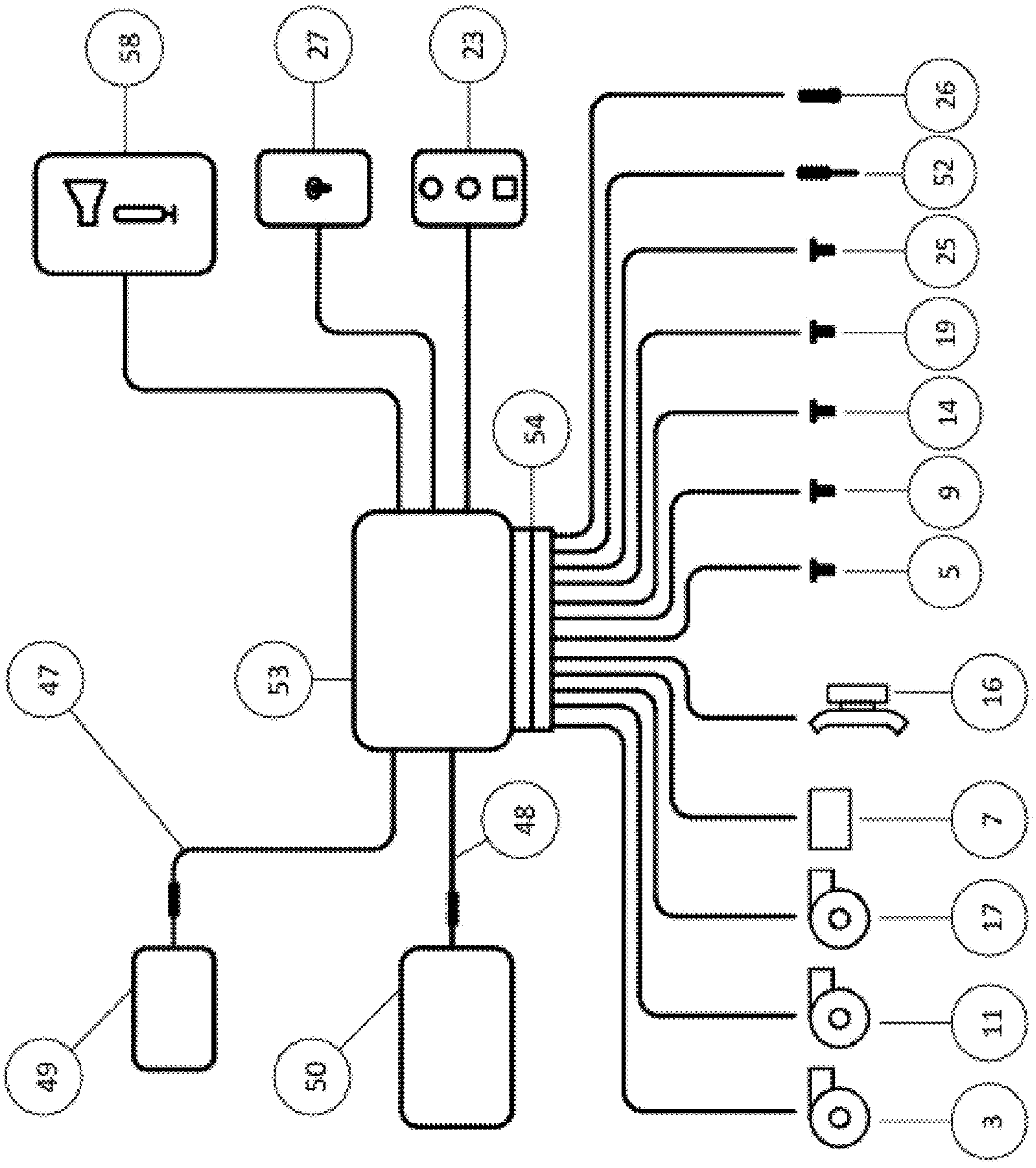
FIG. 7 is an electrical architecture block diagram illustrating the interconnection of various electrical components in a preferred embodiment of the present invention.

The inventions electrical architecture is shown in FIG. 7 in which a central control device (53) is used to ease manufacturability. A central connector (54) is disposed from the central control device (53) to the fans, sensors, and heat pump. Electrical power provided by a battery (50) comes into the central control module via quick disconnect cable (48). The invention is controlled by an on-off switch (27) which is electrically connected to the central control module. A system display of various parameters (23) is driven by information received from the central control module. The communication radio (49) provides audio signals via quick disconnect cable (47) to the central control module which in turn works with the speaker and microphone element (58) inside the helmet. The central control unit receives temperature measurements in the system from five temperature probes (5) (9) (14) (19) (25), one oxygen sensor (52), and one pressure sensor (26) in order to safely control the system. The central control unit hosts algorithms which modulate the power to three fans (3) (11) (17), one PTC Heater (7), and one Peltier solid state heat pump (16).

What is claimed is:

1. A wearable air sterilizer comprising:

a first fan configured to ingest contaminated ambient air and direct said contaminated ambient air through an interconnecting duct;

a PTC heater configured to receive the contaminated ambient air from the first fan through the interconnecting duct and heat the contaminated ambient air above 400 degrees Fahrenheit to create a heated air;

a residence duct configured to receive the heated air, wherein a residence time of the heated air in the residence duct is determined based on a length of the residence duct and a speed of the heated air in the residence duct, in order to sterilize the heated air via physical rupture of a pathogen cell structure to create sterilized heated air;

a first stage of cooling utilizing an air-to-air heat exchanger configured to receive the sterilized heated air from the residence duct and convey the sterilized heated air into a cooling passage which is configured to cool the sterilized heated air to create a lower intermediate temperature sterilized air;

a second fan configured to ingest a second cool, contaminated ambient air and direct said second cool, contaminated ambient air into a heating passage of the air-to-air heat exchanger configured to transfer heat energy from the sterilized heated air to the second cool, contaminated ambient air while maintaining isolation between the sterilized heated air and the second cool, contaminated ambient air;

an intermediate duct providing a structure to isolate and convey the lower intermediate temperature sterilized air from the air-to-air heat exchanger to a second stage of cooling;

the second stage of cooling utilizing a cold side of a Peltier heat pump configured to receive the lower intermediate temperature sterilized air from the intermediate duct and cool the lower intermediate temperature sterilized air by using a third fan configured to ingest a third cool, contaminated ambient air and direct said third cool, contaminated ambient air into a hot side of the Peltier heat pump to transfer heat energy from the lower intermediate temperature sterilized air to the third cool, contaminated ambient air in order to create a cooled sterilized air provided at a comfortable and breathable final air temperature; and a final duct configured for conveying the cooled sterilized air to a wearer.

2. An air sterilizer comprising:

a helmet with a sealed clear visor;

an elastic membrane covering a bottom area of the helmet with an aperture configured for allowing a user's head to pass into the helmet, whereby the elastic membrane is configured to form a seal around the user's neck;

a first fan mounted on said helmet with vibration mounts, and configured to ingest contaminated ambient air and direct said contaminated ambient air through an interconnecting duct;

a PTC heater mounted on said helmet with vibration mounts, and configured to receive the contaminated ambient air from the first fan through the interconnecting duct and heat the contaminated ambient air above 400 degrees Fahrenheit to create a heated air;

a residence duct mounted on said helmet, and configured to receive the heated air, wherein a residence time of the heated air in the residence duct is determined based on a length of the residence duct and a speed of the heated air in the residence duct, in order to sterilize the heated air via physical rupture of a pathogen cell structure to create sterilized heated air;

a first stage of cooling utilizing an air-to-air heat exchanger mounted on said helmet, and configured to receive the sterilized heated air from the residence duct and convey the sterilized heated air into a cooling passage which is configured to cool the sterilized heated air to create a lower intermediate temperature sterilized air;

a second fan mounted on said helmet with vibration mounts, and configured to ingest a second cool, contaminated ambient air and direct said second cool, contaminated ambient air into a heating passage of the air-to-air heat exchanger configured to transfer heat energy from the sterilized heated air to the second cool, contaminated ambient air while maintaining isolation between the sterilized heated air and the second cool, contaminated ambient air;

an intermediate duct mounted on said helmet, and providing a structure to isolate and convey the lower intermediate temperature sterilized air from the air-to-air heat exchanger to a second stage of cooling;

the second stage of cooling utilizing a cold side of a Peltier heat pump mounted on said helmet, and configured to receive the lower intermediate temperature sterilized air from the intermediate duct and cool the lower intermediate temperature sterilized air by using a third fan mounted on said helmet with vibration mounts, and configured to ingest a third cool, contaminated ambient air and direct said third cool, contaminated ambient air into a hot side of the Peltier heat pump to transfer heat energy from the lower intermediate temperature sterilized air to the third cool, contaminated ambient air in order to create a cooled sterilized air provided at a comfortable and breathable final air temperature; and a final duct mounted on said helmet, and configured for conveying the cooled sterilized air into the helmet.

3. An air sterilizer comprising:

a helmet with a sealed clear visor;

an elastic membrane covering a bottom area of the helmet with an aperture configured for allowing a user's head to pass into the helmet, whereby the elastic membrane is configured to form a seal around the user's neck;

a first fan mounted on said helmet with vibration mounts, and configured to ingest contaminated ambient air and direct said contaminated ambient air through an interconnecting duct;

a PTC heater mounted on said helmet with vibration mounts, and configured to receive the contaminated ambient air from the first fan through the interconnecting duct and heat the contaminated ambient air to above 400 degrees Fahrenheit to create a heated air;

a residence duct mounted on said helmet, and configured to receive the heated air, wherein a residence time of the heated air in the residence duct is determined based on a length of the residence duct and a speed of the heated air in the residence duct, in order to sterilize the heated air via physical rupture of a pathogen cell structure to create sterilized heated air;

a first stage of cooling utilizing an air-to-air heat exchanger mounted on said helmet, and configured to receive the sterilized heated air from the residence duct and convey the sterilized heated air into a cooling passage which is configured to cool the sterilized heated air to create a lower intermediate temperature sterilized air;

a second fan mounted on said helmet with vibration mounts, and configured to ingest a second cool, contaminated ambient air and direct said second cool, contaminated ambient air into a heating passage of the air-to-air heat exchanger configured to transfer heat energy from the sterilized heated air to the second cool, contaminated ambient air while maintaining isolation between the sterilized heated air and the second cool, contaminated ambient air;

an intermediate duct mounted on said helmet, and providing a structure to isolate and convey the lower intermediate temperature sterilized air from the air-to-air heat exchanger to a second stage of cooling;

the second stage of cooling utilizing a cold side of a Peltier heat pump mounted on said helmet, and configured to receive the lower intermediate temperature sterilized air from the intermediate duct and cool the lower intermediate temperature sterilized air by using a third fan mounted on said helmet with vibration mounts, and configured to ingest a third cool, contaminated ambient air and direct said third cool, contaminated ambient air through a supply duct into a hot side of the Peltier heat pump to transfer heat energy from the lower intermediate temperature sterilized air to the third cool, contaminated ambient air in order to create a cooled sterilized air provided at a comfortable and breathable final air temperature; and a final duct mounted on said helmet, and configured for conveying the cooled sterilized air into the helmet;

a one-way pressure valve disposed in the helmet, and configured to release air from an inside of the helmet to an ambient environment outside of the helmet at a preset pressure, while preventing contaminated ambient air outside of the helmet to enter the inside of the helmet;

a first temperature sensor configured to measure an ambient air temperature;

a second temperature sensor configured to measure an air temperature of the heated air as it leaves the PTC heater;

a third temperature sensor configured to measure an air temperature of the sterilized heated air as it leaves the air-to-air heat exchanger;

a fourth temperature sensor configured to measure an air temperature of the cooled sterilized air as it leaves the Peltier heat pump;

a fifth temperature sensor configured to measure an air temperature inside the helmet;

an oxygen sensor configured to measure oxygen in the air inside the helmet;

an air pressure sensor configured to measure an air pressure inside the helmet; and a control system configured to use information from the first temperature sensor, the second temperature sensor, the third temperature sensor, the fourth temperature sensor, the fifth temperature sensor, the oxygen sensor, and the air pressure sensor to independently control operation of the first fan, the second fan, the third fan, the PTC heater, and the Peltier heat pump.

4. The air sterilizer of claim 3, wherein electrical power for the first fan, the second fan, the third fan, the PTC heater, the Peltier heat pump, and the control system is provided by at least one rechargeable battery carried on a belt configured to be worn by the user and electrically connected to the helmet via quick disconnect cables.

5. The air sterilizer of claim 3, wherein a flat flexible membrane is disposed in a lower front of the helmet such that one side of the flexible membrane is configured to be exposed to the ambient environment outside of the helmet while an opposite side of the flexible membrane is configured to be exposed to the air inside of the helmet, such that sound energy is configured to be transmitted outside of the helmet.

6. The air sterilizer of claim 3, further comprising a display disposed such that operational parameters are displayed and configured to be visible to the user while wearing the helmet.

7. The air sterilizer of claim 3, further comprising a radio communication system including a radio disposed on a belt configured to be worn by the user, the radio configured to be electrically connected to the helmet via quick disconnect cables.

* * * * *